(12) United States Patent
Mueller et al.

(10) Patent No.: US 10,895,000 B2
(45) Date of Patent: *Jan. 19, 2021

(54) MAGNESIUM ALLOY, METHOD FOR THE PRODUCTION THEREOF AND USE THEREOF

(71) Applicant: BIOTRONIK AG, Buelach (CH)

(72) Inventors: Heinz Mueller, Diedrichshagen (DE); Peter Uggowitzer, Ottenbach (CH); Joerg Loeffler, Greifensee (CH)

(73) Assignee: BIOTRONIK AG, Buelach (CH)

(*) Notice: Subject to any disclaimer, the term of this patent is extended or adjusted under 35 U.S.C. 154(b) by 167 days.

This patent is subject to a terminal disclaimer.

(21) Appl. No.: 14/395,954

(22) PCT Filed: Jun. 20, 2013

(86) PCT No.: PCT/EP2013/062876
§ 371 (c)(1),
(2) Date: Oct. 21, 2014

(87) PCT Pub. No.: WO2014/001191
PCT Pub. Date: Jan. 3, 2014

(65) Prior Publication Data
US 2015/0119995 A1    Apr. 30, 2015

Related U.S. Application Data

(60) Provisional application No. 61/664,229, filed on Jun. 26, 2012.

(51) Int. Cl.
| | |
|---|---|
| *C22C 23/04* | (2006.01) |
| *C22F 1/06* | (2006.01) |
| *C22F 1/00* | (2006.01) |
| *A61L 27/04* | (2006.01) |
| *A61L 27/58* | (2006.01) |
| *C22C 23/02* | (2006.01) |

(52) U.S. Cl.
CPC ............ *C22C 23/04* (2013.01); *A61L 27/047* (2013.01); *A61L 27/58* (2013.01); *C22C 23/02* (2013.01); *C22F 1/00* (2013.01); *C22F 1/06* (2013.01)

(58) Field of Classification Search
CPC ............ C22F 1/06; C22C 23/02; C22C 23/04
USPC ........................................................ 420/405
See application file for complete search history.

(56) References Cited

U.S. PATENT DOCUMENTS

| | | | |
|---|---|---|---|
| 3,320,055 A | 5/1967 | Foerster | |
| 5,055,254 A | 10/1991 | Zuliani | |
| 5,698,158 A * | 12/1997 | Lam | B01D 3/10 |
| | | | 266/149 |
| 8,313,692 B2 * | 11/2012 | Somekawa | C22C 18/00 |
| | | | 420/408 |
| 8,414,717 B2 * | 4/2013 | Buha | C22C 23/00 |
| | | | 148/559 |
| 8,518,102 B2 * | 8/2013 | Kitaoka | A61F 2/91 |
| | | | 623/1.15 |
| 9,072,618 B2 | 7/2015 | Doerr et al. | |
| 9,561,308 B2 | 2/2017 | Schaffer | |
| 9,593,397 B2 | 3/2017 | Imwinkelried et al. | |
| 9,677,151 B2 | 6/2017 | Zuerich | |
| 2008/0031765 A1 | 2/2008 | Gerold et al. | |
| 2009/0171452 A1 | 7/2009 | Yamamoto et al. | |
| 2010/0075162 A1 | 3/2010 | Yang et al. | |
| 2011/0054629 A1 | 3/2011 | Seok et al. | |
| 2011/0076178 A1 | 3/2011 | Somekawa et al. | |
| 2011/0192500 A1 | 8/2011 | Uggowitzer et al. | |
| 2011/0315282 A1 | 12/2011 | Somekawa et al. | |
| 2012/0035740 A1 | 2/2012 | Koo et al. | |
| 2012/0095548 A1 | 4/2012 | Gregorich et al. | |
| 2012/0128997 A1 * | 5/2012 | Numano | B22D 11/001 |
| | | | 428/586 |
| 2012/0269673 A1 | 10/2012 | Koo et al. | |
| 2013/0039805 A1 * | 2/2013 | Somekawa | C22C 23/02 |
| | | | 420/408 |
| 2013/0131814 A1 | 5/2013 | Koo et al. | |
| 2013/0144290 A1 | 6/2013 | Schiffl | |
| 2013/0315282 A1 | 11/2013 | Mayer | |
| 2014/0065009 A1 | 3/2014 | Imwinkelried et al. | |
| 2014/0261911 A1 | 9/2014 | Imwinkelried et al. | |
| 2015/0047756 A1 | 2/2015 | Washio et al. | |

(Continued)

FOREIGN PATENT DOCUMENTS

| | | |
|---|---|---|
| CN | 1743486 A | 3/2006 |
| CN | 1792383 | 6/2006 |

(Continued)

OTHER PUBLICATIONS

NPL: On-line English translation of CN 101948957A, Jan. 2011 (Year: 2011).*
Chen, Ji-Hua, et al., "Microstructural stability and mechanical properties of Mg—Zn—Al alloys", Hunan-Daxue-Xuebao / Ziran-Kexue-Ban =Journal of Hunan University/ Hunan Daxue Zhuban, vol. 34, No. 1, Jan. 1, 2007, pp. 47-51.
Friedrich, Horst, E., et al., "Magnesium Technology", Jan. 1, 2006 (Jan. 1, 2006), Springer, Berlin Heidelberg New York, pp. p. 231-232; p. 289-301; p. 308-315.

(Continued)

*Primary Examiner* — Jie Yang
(74) *Attorney, Agent, or Firm* — Greer, Burns & Crain, Ltd.; Steven P. Fallon

(57) ABSTRACT

A magnesium alloy, implants and method for the production thereof. The magnesium alloy includes 1.5 to 7.0% by weight Zn, 0.5 to 3.5% by weight Al, the remainder being magnesium which contains impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P.

19 Claims, No Drawings

(56) References Cited

U.S. PATENT DOCUMENTS

| | | |
|---|---|---|
| 2015/0080938 A1 | 3/2015 | Groff |
| 2015/0080998 A1* | 3/2015 | Mueller .................. C22C 23/02 623/1.1 |
| 2015/0119995 A1 | 4/2015 | Mueller et al. |
| 2015/0129091 A1 | 5/2015 | Mueller et al. |
| 2015/0129092 A1 | 12/2015 | Mueller et al. |
| 2016/0022876 A1 | 1/2016 | Imwinkelried et al. |

FOREIGN PATENT DOCUMENTS

| | | | |
|---|---|---|---|
| CN | 1792384 | A | 6/2006 |
| CN | 101629260 | A | 1/2010 |
| CN | 101658691 | | 3/2010 |
| CN | 101308105 | B | 8/2010 |
| CN | 101899600 | A | 12/2010 |
| CN | 101948957 | A * | 1/2011 |
| CN | 102312144 | | 1/2012 |
| DE | 1483204 | | 10/1969 |
| DE | 102006060501 | A1 | 6/2008 |
| DE | 102010027532 | B4 | 6/2014 |
| EP | 0295397 | A1 | 12/1988 |
| EP | 1959025 | A1 | 8/2008 |
| EP | 2295613 | A1 | 3/2011 |
| EP | 2384725 | | 11/2011 |
| EP | 2384725 | A1 | 11/2011 |
| EP | 2085100 | B1 | 1/2015 |
| JP | 02047238 | | 2/1990 |
| JP | 07018364 | | 1/1995 |
| JP | H11502565 | A | 3/1999 |
| JP | 2010163635 | | 7/2010 |
| JP | 2010529288 | | 8/2010 |
| JP | 2011502565 | A | 1/2011 |
| JP | 2012082474 | | 4/2012 |
| NO | 2007058276 | A1 | 5/2007 |
| NO | 2009148093 | A1 | 12/2009 |
| NO | 2010082669 | A1 | 7/2010 |
| NO | 2011051424 | A1 | 5/2011 |
| RU | 2098506 | | 12/1997 |
| RU | 2437949 | | 12/2011 |
| WO | 9626297 | A1 | 8/1996 |
| WO | 1997040201 | | 10/1997 |
| WO | 2004013364 | | 2/2004 |
| WO | 2005108634 | | 11/2005 |
| WO | 2007058276 | A1 | 5/2007 |
| WO | 2008016150 | | 2/2008 |
| WO | 2009147861 | | 12/2009 |
| WO | 2009148093 | A8 | 12/2009 |
| WO | 2010082669 | A1 | 7/2010 |
| WO | 2011051424 | A1 | 5/2011 |
| WO | 2011114931 | | 9/2011 |
| WO | 2011114931 | A1 | 9/2011 |
| WO | 2012003522 | | 1/2012 |
| WO | 2013107644 | | 7/2013 |
| WO | 2014001321 | | 1/2014 |
| WO | 2014159328 | | 10/2014 |

OTHER PUBLICATIONS

Geis-Gerstorfer, J., et al., "Blood triggered corrosion of magnesium alloys", Materials Science and Engineering B, vol. 176, (2011), pp. 1761-1766.
Kim, Ye-Lim, et al., "Effect of Al Addition on the Precipitation Behavior of a Binary Mg—Zn", Kor. J. Mater. Res., vol. 22, No. 3, (2012), pp. 111-117.
Liu, Qiang, et al., "Influences of Al on Microstructures and Properties of Mg-6Zn Alloys", Kuangye-Gongcheng =Mining and Metallurgical Engineering, vol. 25, No. 5, Oct. 1, 2005, pp. 74-76.
Zou, H., et al., "Effects of Nd on the Microstructure and Mechanical Property of ZA52 Alloy", Materials Science Forum, vols. 488-489, (2005), pp. 161-164.
Zou, H., et al., Effects of microstructure on creep behavior of Mg—5%Zn—2%Al(-2%Y) alloy, Trans. Nonferrous Met. Soc. China, vol. 18, No. 3, (Jun. 2008), pp. 580-587.
Radeck, Stephanie, "International Search Report" Patent Cooperation Treaty Application No. PCT/EP2013/062876, European Patent Office as International Search Authority, dated Oct. 16, 2013, 5 pages.
Wang, Haining, "Notification of the First Office Action", Chinese Patent Application 201380022714.6, dated Mar. 9, 2016, 7 pages.
He, You li an, et al., "Production of Very Fine Grained Mg—3% Ai—1%Zn Alloy by Continuous Extrusion Forming (Conform)", Advanced Engineering Materials, 12, No. 9, (2010), pp. 843-847.
Hillis et al., "Compositional Requirements for Quality Performance with High Purity," International Magnesium Association Meeting; 55th, International Magnesium Association, (1998), pp. 74-81.
Jin, Li, et al., "Mechanical properties and microstructure of AZ31 Mg alloy processed by two-step equal channel angular extrusion", Materials Letters, 59, (2005), pp. 2267-2270.
JP Office Action for Application No. 2015519055, dated Jun. 1, 2017.
Kammer, Catrin, et al., "Magnesium Taschenbuch", Aluminium-Verlag, Duesseldorf (2000), pp. 156-161.
Kammer, Catrin, et al., "Magnesium Taschenbuch", Aluminium-Verlag, Duesseldorf (2000), pp. 156-161 (English language machine translation).
Kannan et al., Evaluating the stress corrosion crackihnhg susceptibility of Mg—Al—Zn alloy in modified-simulated body fluid for orthopaedic implant application, Scripta Materialia, 59 (2008) pp. 175-178.
Li Xuesong, et al., "Microstructure, mechanical properties and corrosion behavior of Mg-1Zn-0.5Ca alloy", Advanced Materials Research, Trans Tech Publications Ltd., vol. 311-313, Jan. 1, 2011, pp. 1735-1740.
Martienssen, Werner, et al, "Springer Handbook of Condensed Matter and Materials Data—Part 3.1", Springer-Verlag Berlin Heidelberg, New York, (2005), pp. 160-170 and cover pages (23 pages).
Oh J.C., et al., "TEM and 3DAP characterization of an age-hardened Mg—Ca—Zn alloy", Scripta Materialia, vol. 53, No. 6 Sep. 1, 2005, pp. 675-679.
Oh-Ishi, K., et al., "Influence of Zn additions on age hardening response and microstructure of Mg-0.3at.% Ca alloys", Magnesium Technology 2010, "Proceedings of a Symposium Held During [the] TMS Annual Meeting & Exhibition," Jan. 1, 2010, pp. 517-520.
Oh-Ishi, K., et al., "Age-hardening response of Mg-0.3 at %Ca alloys with different Zn contents," Materials Science and Engineering, A: vol. 526, Nos. 1-2, Nov. 25, 2009, pp. 177-184.
Radeck, Stephanie, "International Search Report and Written Opinion of the International Searching Authority", Patent Cooperation Treaty Application PCT/EP2013/063253, European Patent Office as International Search Authority, Search Completed Sep. 26, 2013, International Search Report dated Oct. 4, 2013, 13 pages.
Radeck, Stephanie, "International Search Report and Written Opinion of the International Searching Authority", Patent Cooperation Treaty Application PCT/EP2013/063110, European Patent Office as International Search Authority, Search Completed Oct. 1, 2013, International Search Report dated Dec. 2, 2013, 10 pages.
Radeck, Stephanie, "Office Action" for EP Office Action Application No. 13730893.8, dated Apr. 19, 2017.
Radeck, Stephanie, "Office Action" for EP Office Action Application No. 13731134.6, dated Apr. 19, 2017.
Radeck, Stephanie, "Office Action" for EP Office Action Application No. 13729770.0, dated Apr. 19, 2017.
Radeck, Stephanie, "Office Action" for EP Office Action Application No. 13730613.0, dated Apr. 19, 2017.
RU Office Action for Application No. 2015101291/02, dated Jun. 2, 2017.
RU Office Action for Application No. 2015102166/02, dated Jun. 2, 2017.
RU Office Action for Application No. 2015102168/02, dated Jun. 2, 2017.
Schuetze, Michael, et al., "Fundamentals of High Temperature Corrosion", Materials Science and Technology, Wiley-VCH Verlag GmbH, 2000, pp. 67-129.

(56) References Cited

OTHER PUBLICATIONS

Somekawa, H., et. al., "High strength and fracture toughness balance on the extruded Mg—Ca—Zn alloy", Materials Science and Engineering: A, vol. 459, Nos. 1-2, Jun. 25, 2007, pp. 366-370.
Song, G., et al., "Corrosion of Non-Ferrous Alloys. III. Magnesium Alloys", Materials Science and Technology, Wiley-VCH Verlag GmbH, 2000, pp. 131-171.
Sun, Yu, et al., "Preparation and characterization of a new biomedical MgZnCa alloy", Materials and Design, vol. 34, Jul. 23, 2011, pp. 58-64.
Wang, Jinyong, "Notification of the First Office Action," Chinese Patent Application No. 201380022063.0, dated Feb. 1, 2016, 10 pages.
Wang, Xi-Shu, et al., "Effect of equal channel angular extrusion process on deformation behaviors of Mg—3Al—Zn alloy", Materials Letters, 62, (2008), pp. 1856-1858.
Wenjiang, Ding, "Science and Technology of Magnesium Alloys," Science Publishing House, Jan. 2007, pp. 323-324.
Xie, Yang, State Intellectual Property Office of the People's Republic of China Notification of the First Office Action, Application No. 201380022716.5, dated Mar. 3, 2016, 11 pages.
Xu, Bingshe et al., "1200 questions on nonferrous metallurgy," 747. How to prepare highly pure magnesium, Chemical Industry Press, p. 252.
Xu, Yang, State Intellectual Property Office of the People's Republic of China Notification of the First Office Action, Application No. 201380022712.7, dated Feb. 29, 2017, 8 pages.
Xu, Yang, State Intellectual Property Office of the People's Republic of China Notification of the Second Office Action, Application No. 201380022712.7, dated Nov. 18, 2016, 10 pages.
Xu, Yang, State Intellectual Property Office of the People's Republic of China Notification of the Third Office Action, Application No. 201380022712.7, dated May 25, 2017, 10 pages.
Yang, M.B., et al., "Comparison of as-cast microstructures and solidification behaviours of Mg—Zn—Al ternary magnesium alloys with different Zn/Al mass ratios," Advanced Materials Research, Trans Tech Publications Ltd., vol. 548, Jan. 1, 2012, pp. 321-327.
Zhang, B.P., et al., "Enhanced mechanical properties in fine-grained Mg—1.0Zn—0.5Ca alloys prepared by extrusion at different temperatures", Scripta Materialia, vol. 63, No. 10, Nov. 1, 2010, pp. 1024-1027.
Zou, Hong-hui, "Effects of microstructure on creep behavior of Mg—5%Zn—2%(-2%YY) alloy", Trans. Nonferrous Met. Soc. China, vol. 18, (2008), pp. 580-587.
Kawamura, Yuji, et al., "Office Action" Japanese Patent Application No. 2015-518992, dated May 30, 2017, (15 pages).
Kannan et al., Evaluating the stress corrosion crackihnhg susceptibility of Mg—Al—Zn alloy in modified-simulated body fluid for orthopaedic implant application, Scripts Materialia, 59 (2008) pp. 175-178.
Li Xuesong, et al., "Microstructure, mechanical properties and corrosion behavior of Mg—1.2n—0.5Ca alloy", Advanced Materials Research, Trans Tech Publications Ltd., vol. 311-313, Jan. 1, 2011, pp. 1735-1740.
Oh, J.C., et al., "TEM and 3DAP characterization of an age-hardened Mg—Ca—Zn alloy", Scripta Materialia, vol. 53, No. 16, Sep. 1, 2005, pp. 675-679.
Zhang, B.P., et al., "Enhanced mechanical properties in fine-grained Mg—1.0Zn—0.5Ca alloys prepared by extrusion at different temperatures", Scripts Materialia, vol. 63, No. 10, Nov. 1, 2010, pp. 1024-1027.
Bakhsheshi-Rad, et al., Characterization and Corrosion Behavior of Biodegradable Mg—Ca and Mg—Ca—Zn Implant Alloys, Appl. Mech. Mater, Jan. 2012, 121-126, 568-572 (Abstract Only).
Sun, Yu, et al., Preparation and Characterization of a New Biomedical Mg—Zn—Ca Alloy, Materials and Design, vol. 34, pp. 56-64, Feb. 2012 (Abstract Only).
Koike, Junichi, Dislocation Plasticity and Complementary Deformation Mechanisms in Polycrystalline Mg Alloys, Mater. Sci. Forum, Mar. 2004, 4999-452, 665-668 (Abstract Only).

Wilson, D.V., et al., Effects of Preferred Orientation on the Grain Size Dependence of Yield Strength in Metals, Philos. Mag., Jun. 1963, 1543-1551 (Abstract Only).
L'Ecuyer, J.D., et al., Precipitation Interactions with Dynamic Recrystallization of HSLS Steel, Acta Metallurigica, Apr. 1989, 37, 4, 1023-1031 (Abstract Only).
International Search Report for PCT/US2014/023047, dated Jan. 31, 2014.
International Search Report for PCT/US2013/057294, dated Jun. 17, 2014.
Xu, Bingshe, et al., 1200 Questions on Nonferrous Metallurgy; 747, How to Prepare Highly Pure Magnesium, Jan. 1, 2008.
ASTM International, Standard Specification for Magnesium-Alloy Die Castings, 1998.
European Committee for Standardization, Magnesium and Magnesium Alloys, 1998.
Hanawalt, et al., Corrosion Studies of Magnesium and Its Alloys, Metals Technology, Sep. 1941, 273-299.
Li, Wen, et al., Preparation and in Vitro Degradation of the Composite Coating with High Adhesion Strength on Biodegradable Mg—Zn, Ca Alloy, Materials Characterization 62 (2011), 1158-1165.
Cha, Pil-Ryung, et al., Biodegradability Engineering of Biodegradable Mg Alloys: Tailoring the Electrochemical Properties and Microstructure of Constituent Phases, Scientific Reports 3:2367, 1-6, 2013.
Song, Yingwei, et al., The Role of Second Phases in the Corrosion Behavior of Mg—5ZN Alloy, Corrosion Science 60 (2012) 238-245.
Abidin, nor Ishida Zainal, et al., Corrosion of High Purity Mg, Mg2Zn0.2Mn,ZE41 and AZ91 in Hank's Solution at 37° C, Corrosion Science 53 (2011) 3542-3556.
Bakhsheshi-Rad, H.R., et al., Relationship Between the Corrosion Behavior and the Thermal Characteristics and Microstructure of Mg—0.5Ca—xZn Alloys, Corrosion Science 64 (2012) 184-197.
Sugiura, Tsutomu, et al., A Comparative Evaluation of Osteosynthesis with Lag Screws, Miniplates, or Kirschner Wires for Mandibular Condylar Process Fractures, J. Oral Maxillofac Surg 59:1161-1168, 2001.
Manohar, P.A., et al., Five Decades of the Zenar Equation, ISIJ International, vol. 38 (1998), No. 9, pp. 913-924.
Wang, Bin, et al., Biocorrosion of Coated Mg—Zn—Ca Alloy under Constant Compressive Stress Close to that of Human Tibia, Materials Letters 70 (2012) 174-176.
Barnett, M.R., et al., Influence of Grain Size on the Compressive Deformation of Wrought Mg—3Al—1Zn, Acta Materiala 52 (2004) 5093-5103.
Du, Hui, et al., Effects of Zn on the Microstructure, Mechanical Property and Bio-Corrosion Property of Mg—3Ca Alloys for Biomedical Application, Materials Chemistry and Physics 125 (2011) 568-575.
Kirkland, Nicholas, et al., In Vitro Dissolution of Magnesium-Calcium Binary Alloys: Clarifying the Unique Role of Calcium Additions in Bioresorbable Magnesium Implant Alloys, Wiley Online Library, 2010, 91-100.
Zhang, Erlin, et al., Microstructure, Mechanical Properties and Bio-Corrosion Properties of Mg—Zn—Mn—Ca Alloy for Biomedical Application, Materials Science and Engineering A 497 (2008) 111-118.
Song, Guang Ling, et al., Understanding Magnesium Corrosion, A Framework for Improved Alloy Performance, Advanced Engineering Materials, 2003, 5, No. 12, 837-858.
Song, Guang Ling, et al., Corrosion Mechanisms of Magnesium Alloys, Advanced Engineering Materials, 1999, 1, No. 1, 11-33.
Abidin, Nor Ishida Zainal et a.., The In Vivo and in Vitro Corrosion of High-Purity Magnesium and Magnesium Alloys WZ21 and AZ91, Corrosion Science 75 (2013) 354-366.
Kirkland, N.T., et al., Assessing the Corrosion of Biodegradable Magnesium Implants: A Critical Review of Current Methodologies and Their Limitations, Acta Biomaterialia 8 (2012) 925-936.
Kirkland, Nicholas T., et al., Buffer-Regulated Biocorrrosion of Pure Magnesium, J. Mater Sci: Mater Met (2012) 23: 283-291.

(56) References Cited

OTHER PUBLICATIONS

Hanzi, Anja C., et al., On the In Vitro and In Vivo Degradation Performance and Biological Response of New Biodegradable Mg—Y—Zn Alloys, Acta Biomateriala 6 (2010) 1824-1833.
Yamamoto, Akiko, et al., Effect of Inorganic Salts, Amino Acids and Proteins on the Degradation of Pure Magnesium in Vitro, Materials Science and Engineering C 29 (2009) 1559-1568.
Cao, Fuyong, et al., Corrosion of Ultra-High-Purity Mg in 3.5% NaCl Solution Saturated with Mg(OH)2, Corrosion Science 75 (2013) 78-99.
Kalb, H., et al., Impact of Microgalvanic Corrosion on the Degradation Morphology of WE43 and Pure Magnesium under Exposure to Simulated Body Fluid, Corrosion Science 57 (2012) 122-130.
Schinhammer, Michael, et al., On the Immersion Testing of Degradable Implant Materials in Simulated Body Fluid: Active pH Regulation Using CO2, Advanced Engineering Materials, 2013, 15, No. 6, 434-441.
Liu, Ming, et al., Calculated Phase Diagrams and the Corrosion of Die-Cast Mg—Al Alloys, Corrosion Science, 2009, 602-619.
Pilcher, Karin, et al., Immunological Response to Biodegradable Magnesium Implants, JOM, vol. 66, No. 4, 2014.
Kraus, Tanja, et al., Magnesium Alloys for Temporary Implants in Osteosynthesis: In Vivo Studies of their Degradation and Interaction with Bone, Acta Biomaterialia 8 (2012) 1230-1238.
Homma, T., et al., Effect of Zr Addition on the Mechanical Properties of As-Extruded Mg—Zn—Ca—Zr Alloys, Materials Science and Engineering A 527 (2010) 2356-2362.
Mendis, C.L., et al., Precipitation-Hardenable Mg—2.4Zn—0.1Ag—0.1Ca—0.16Zr (at.%) Wrought Magnesium Alloy, Acta Materialia 57 (2009) 749-760.
Koike, J., et al., The Activity of Non-Basal Slip Systems and Dynamic Recovery at Room Temperature in Fine-Grained AZ31B Magnesium Alloys, Acta Materialia 51 (2003) 2055-2065.
Hanzi, A.C., et al., Design Strategy for Microalloyed Ultra-Ductile Magnesium Alloys, Philosophical Magazine Letters, vol. 89, No. 6, Jun. 2009, 377-390.
Bamberger, M., et al., Trends in the Development of New Mg Alloys, Annu. Rev. Mater. Res. 2008, 38:505-33.
Farahany, Saeed, et al., In-Situ Thermal Analysis and Macroscopical Characterization of Mg—xCa and Mg—0.5Ca—xZn Alloy Systems, Thermochimica Acta 527 (2012) 180-189.
Zhang, Baoping, et al., Mechanical Properties, Degradation Performance and Cytotoxicity of Mg—Zn—Ca Biomedical Alloys with Different Compositions, Materials Science and Engineering C 31 (2011) 1667-1673.
Gunde, P., et al., High-Strength Magnesium Alloys for Degradable Implant Applications, Materials Science and Engineering,A 528 (2011) 1047-1054.
Stefanidou, M. et al., Zinc: A Multipurpose Trace Element, Arch Toxicol (2006) 80: 1-9.
Tapiero, Haim, et al., Trace Elements in Human Physiology and Pathology: Zinc and Metallothioneins, Biomedicine & Pharmacotherapy 57 (2003) 399-411.
Hanzi, A.C., et al., Design Considerations for Achieving Simultaneously High-Strength and Highly Ductile Magnesium Alloys, Philosophical Magazine Letters 2012, 1-11.
Zberg, Bruno, et al, MgZnCa Glasses Without Clinically Observable Hydrogen Evolution for Biodegradable Implants, Nature Materials, vol. 8, Nov. 2009, 887-891.
Staiger, Mark P., et al., Magnesium and its Alloys as Orthopedic Biomaterials: A Review, Biomaterials 27 (2006) 1728-1734.
Witte, Frank, et al., Degradable Biomaterials Based on Magnesium Corrosions, Current Opinion in Solid State and Materials Science (2009).
Zhang, Shaoxiang, et al., Research on an Mg—Zn Alloy as Degradable Biomaterial, Acta Biomaterialia 6 (2010) 626-640.
Song, Guangling, Control of Biodegradation of Biocompatable Magnesium Alloys, Corrosion Science 49 (2007) 1696-1701.
Hofstetter, J., et al., High-Strength Low-Alloy (HSLA) Mg—Zn—Ca Alloys with Excellent Biodegradation Performance, JOM, vol. 66, No. 4, 2014.
Mendis, C.L., et al., An Enhanced Age Hardening Response in Mg—Sn Based Alloys Containing Zn, Materials Science and Engineering A 435-436 (2006) 163-171.
Sudholz, A.D., et al., Corrosion Behaviour of Mg-Alloy AZ91E with Atypical Alloying Additions, Journal of Alloys and Compounds 471 (2009) 109-115.
Chia, T.L., et al., The Effect of Alloy Composition on the Microstructure and Tensile Properties of Binary Mg-rare Earth Alloys, Intermetallics 17 (2009) 481-490.
Birbilis, N., et al., On the Corrosion of Binary Magnesium-Rare Earth Alloys, Corrosion Science 51 (2009) 683-689.
Birbilis, N., et al., A Combined Neural Network and Mechanistic Approach for the Prediction of Corrosion Rate and Yield Strength of Magnesium-Rare Earth Alloys, Corrosion Science 53 (2011) 168-176.
A.D. Sudholz, et al., Electrochemical Properties of Intermetallic Phases and Common Impurity Elements in Magnesium Alloys, Electrochemical and Solid-State Letters, 14 (2) C5-C7 (2011).
Shaw, Barbara, Corrosion Resistance of Magnesium Alloys, ASM Handbook, vol. 13A, 2003,692-696.
Zou, "Effects of microstructure on creep behavior of Mg—5%Zn—2%Al (-2%Y) alloy", Transactions of Nonferrous Metals Society of China, vol. 18, pp. 580-587, 2008.
Kawamura, Japanese Office Action for corresponding Japanese Application No. 2015-518992, dated Apr. 11, 2018.

\* cited by examiner

MAGNESIUM ALLOY, METHOD FOR THE PRODUCTION THEREOF AND USE THEREOF

PRIORITY CLAIM

This application is a U.S. National Phase under 35 U.S.C. § 371 of International Application No. PCT/EP2013/062867, filed Jun. 20, 2013, which claims priority to U.S. Provisional Application No. 61/664,229, filed Jun. 26, 2012.

FIELD OF THE INVENTION

A field of the invention relates to a magnesium alloy and to a method for the production thereof and to the use thereof. Magnesium alloys of the invention are applicable to implants, including cardiovascular, osteosynthesis, and tissue implants. Example applications include stents, valves, closure devices, occluders, clips, coils, staples, implantable regional drug delivery devices, implantable electrostimulators (like pacemakers and defibrillators), implantable monitoring devices, implantable electrodes, systems for fastening and temporarily fixing tissue implants and tissue transplantations. Additional example applications include implantable plates, pins, rods, wires, screws, clips, nails, and staples.

BACKGROUND

Magnesium alloy properties are determined by the type and quantity of the alloying elements and impurities as well as the production conditions. The effects of the alloying elements and impurities on the properties of the magnesium alloys have been known to artisans. However, determining the properties of binary or ternary magnesium alloys for the use thereof as implant materials remains complex.

The alloying element used most frequently for magnesium is aluminum, resulting in increased tensile strength due to solid solution and precipitation hardening and fine grain formation, but also in microporosity. Moreover, in the melt aluminum shifts the iron precipitation boundary toward drastically lower iron contents at which the iron particles precipitate or form intermetallic particles together with other elements.

Undesirable accompanying elements in magnesium alloys include iron, nickel, cobalt and copper, which cause a considerable increase in the corrosion tendency due to the electropositive nature thereof.

Manganese can be found in all magnesium casting alloys and binds iron in the form of AlMnFe precipitations, whereby the formation of local elements is reduced. On the other hand, manganese is not able to bind all the iron, and therefore a remainder of iron and a remainder of manganese are always left in the melt.

Silicon lowers the castability and viscosity, and as the content of Si rises, a worsened corrosion behavior is to be expected. Iron, manganese and silicon have a very high tendency to form an intermetallic phase. The electrochemical potential of this phase is very high and can thus act as a cathode controlling the corrosion of the alloy matrix.

As a result of solid solution hardening, zinc improves the mechanical properties and results in grain refining, however it also leads to microporosity with a tendency toward hot cracking starting at a content of 1.5 to 2% by weight in binary Mg—Zn and ternary Mg—Al—Zn alloys.

Alloying additions made of zirconium increase the tensile strength without lowering the expansion and lead to grain refining, but also to a strong impairment of dynamic recrystallization, which is manifested in an increase of the recrystallization temperature and therefore requires high energy expenditure. Moreover, zirconium cannot be added to melts containing aluminum and silicon because the grain refining effect is lost.

Rare earths such as Lu, Er, Ho, Th, Sc and In all exhibit a similar chemical behavior and form eutectic systems with partial solubility on the magnesium-rich side of the binary phase diagrams such that precipitation hardening is possible.

The addition of further alloying elements, in conjunction with the impurities, is known to cause the formation of different intermetallic phases in binary magnesium alloys. For example, the intermetallic phase $Mg_{17}Al_{12}$ forming on the grain boundaries is brittle and limits the ductility. As compared to the magnesium matrix, this intermetallic phase is more noble and able to form local elements, whereby the corrosion behavior worsens.

In addition to these influencing factors, the properties of the magnesium alloys also decisively depend on the metallurgical production conditions. Conventional casting methods automatically introduce impurities when adding, by alloying, the alloying elements. The prior art (U.S. Pat. No. 5,055,254 A) therefore defines tolerance limits for impurities in magnesium casting alloys, which, for example for a magnesium-aluminum-zinc alloy containing approximately 8 to 9.5% by weight Al and 0.45 to 0.9% by weight Zn, mentions tolerance limits of 0.0015 to 0.0024% by weight Fe, 0.0010% by weight Ni, 0.0010 to 0.0024% by weight Cu and no less than 0.15 to 0.5% by weight Mn.

Tolerance limits for impurities in magnesium and the alloys thereof as well as the production conditions are mentioned in many known documents and listed as follows in % by weight:

| Alloy | Production | State | Fe | Fe/Mn | Ni | Cu |
|---|---|---|---|---|---|---|
| Pure Mg | no information | | 0.017 | | 0.005 | 0.01 |
| AZ 91 | Die casting | F | | 0.032 | 0.005 | 0.040 |
| | High-pressure die casting | | | 0.032 | 0.005 | 0.040 |
| | Low-pressure die casting | | | 0.032 | 0.001 | 0.040 |
| | | T4 | | 0.035 | 0.001 | 0.010 |
| | | T6 | | 0.046 | 0.001 | 0.040 |
| | Gravity die casting | F | | 0.032 | 0.001 | 0.040 |
| AM60 | Die casting | F | | 0.021 | 0.003 | 0.010 |
| AM50 | Die casting | F | | 0.015 | 0.003 | 0.010 |
| AS41 | Die casting | F | | 0.010 | 0.004 | 0.020 |
| AE42 | Die casting | F | | 0.020 | 0.020 | 0.100 |

It has been found that these tolerance definitions are not sufficient to reliably exclude the formation of corrosion-promoting intermetallic phases, which in terms of electrochemistry have a more noble potential than the magnesium matrix.

Biodegradable implants (orthopedics, traumatology, cardiovascular implants) require a load-bearing function and consequently strength, together with sufficient expandability, during the physiologically necessary support periods thereof. Known magnesium materials fail to provide the strength properties provided by permanent implants made from other materials such as titanium, CoCr alloys and titanium alloys. The ultimate tensile strength $R_m$ for permanent implants is approximately 500 MPa to >1000 MPa, while that of magnesium materials is <275 MPa so far, and in most cases <250 MPa.

Another drawback of many prior magnesium materials is that the difference between ultimate tensile strength $R_m$ and proof stress $R_p$ is small. In the case of implants that allow plastic deformation, such as cardiovascular stents, this means that no further resistance exists against deformation after initial deformation of the material, and the regions that have already been deformed are deformed further without any load increase. This can lead to overstretching of parts of the component and fracture may occur.

Many magnesium materials, such as the alloys containing 3 to 10% by weight Al and less than 1% by weight Zn and Mn (AZ group), for example, additionally exhibit a clearly pronounced mechanical asymmetry, which is manifested in the difference in the mechanical properties, especially the proof stress $R_p$ with tension load and compression load. Such asymmetries are created, for example, during forming processes such as extrusion, rolling and drawing, which are used to produce suitable semi-finished products. A difference between the proof stress $R_p$ during tension and the proof stress $R_p$ during compression that is too large may result in inhomogeneous deformation of a component, such as a cardiovascular stent, which later undergoes multiaxial deformation, and may cause cracking and fracture.

Because of the low number of crystallographic slip systems, magnesium alloys can generally also form textures during forming processes such as extrusion, rolling and drawing used to produce suitable semifinished products by orienting the grains during the forming process. Specifically, this means that the semifinished product has different properties in different directions in space. For example, high deformability or elongation at fracture occurs in one direction in space after forming, and reduced deformability or elongation at fracture occurs in another direction in space. The formation of such textures should likewise be avoided, because a stent is subjected to high plastic deformation, and reduced elongation at fracture increases the risk of failure of the implant. One method for substantially avoiding such textures during forming is to adjust as fine a grain as possible prior to forming. Because of the hexagonal lattice structure of magnesium materials, the ability of these materials to deform at room temperature is low, which is characterized by slip in the base plane. If the material additionally has a coarse microstructure, i.e., a coarse grain, so-called twinning is forcibly produced upon further deformation, at which shear strain occurs, which transforms a crystal region into a position that is mirror symmetrical to the starting position. The resulting twin grain boundaries constitute weak points in the material, where incipient cracking starts, especially with plastic deformation, which ultimately leads to the destruction of the component.

The resulting twin grain boundaries constitute weak points in the material, where incipient cracking starts, especially with plastic deformation, which ultimately leads to the destruction of the component.

If the grain of the implant materials is sufficiently fine, the risk of such implant failure is drastically reduced. Implant materials should therefore have as fine a grain as possible so as to prevent such undesirable shear strain.

All available magnesium materials for implants are subject to high corrosion in physiological media. Attempts have been made to curb the corrosion tendency by providing the implants with a corrosion-inhibiting coating, for example made of polymeric materials (EP 2 085 100 A2, EP 2 384 725 A1), an aqueous or alcoholic conversion solution (DE 10 2006 060 501 A1) or an oxide (DE 10 2010 027 532 A1, EP 0 295 397 A1).

The polymeric passivation layers are controversial, because virtually all appropriate polymers also cause strong inflammations in the tissue at times. On the other hand, thin magnesium alloy structures without such protective measures do not resist corrosions for the required support periods. The corrosion on thin-walled traumatological implants is often times accompanied by an excessively fast loss of tensile strength, which poses an additional burden by forming excessive amounts of hydrogen per unit of time. The consequences are undesirable gas inclusions in the bones and tissue. In the case of traumatological implants having larger cross-sections, there is a need to be able to deliberately control the hydrogen problem and the corrosion rate of the implant by way of the structure thereof.

Specifically with biodegradable implants, there is a desire for maximum biocompatibility of the elements, because all the chemical elements that are contained are absorbed by the body after decomposition. In any case, highly toxic elements such as Be, Cd, Pb, Cr and the like should be avoided.

Degradable magnesium alloys are especially suitable for implementing implants which have been employed in a wide variety of forms in modern medical technology. Implants are used, for example, to support vessels, hollow organs and vein systems (endovascular implants, such as stents), for fastening and temporarily fixing tissue implants and tissue transplantations, but also for orthopedic purposes, such as nails, plates or screws. A particularly frequently used form of an implant is the stent.

The implantation of stents has become established as one of the most effective therapeutic measures for the treatment of vascular diseases. Stents have the purpose of assuming a supporting function in hollow organs of a patient. For this purpose, stents featuring conventional designs have a filigree supporting structure comprising metal struts, which is initially present in compressed form for introduction into the body and is expanded at the site of the application. One of the main application areas of such stents is to permanently or temporarily widen and hold open vascular constrictions, particularly constrictions (stenosis) of coronary blood vessels. In addition, aneurysm stents are known, which are used primarily to seal the aneurysm. The support function is additionally provided.

A stent has a base body made of an implant material. An implant material is a non-living material, which is employed for applications in medicine and interacts with biological systems. A basic prerequisite for the use of a material as an implant material, which is in contact with the body environment when used as intended, is biocompatibility. For the purpose of the present application, biocompatibility shall be understood to mean the ability of a material to induce an appropriate tissue reaction in a specific application. This includes an adaptation of the chemical, physical, biological, and morphological surface properties of an implant to the recipient's tissue with the aim of a clinically desired interaction. The biocompatibility of the implant material is also dependent on the temporal process of the reaction of the biosystem in which it is implanted. For example, irritations and inflammations occur in a relatively short time, which can lead to tissue changes. Depending on the properties of the implant material, biological systems thus react in different ways. According to the reaction of the biosystem, the implant materials can be divided into bioactive, bioinert and degradable or resorbable materials.

Conventional implant materials include polymers, metallic materials, and ceramic materials (as coatings, for example). Biocompatible metals and metal alloys for permanent implants include, for example, stainless steels (such as 316L), cobalt-based alloys (such as CoCrMo cast alloys, CoCrMo forge alloys, CoCrWNi forge alloys and CoCrNiMo forge alloys), pure titanium and titanium alloys (such as cp titanium, TiAl6V4 or TiAl6Nb7) and gold alloys. In the field of biocorrodible stents, the use of magnesium or pure iron as well as biocorrodible base alloys of the elements magnesium, iron, zinc, molybdenum, and tungsten have been proposed.

The use of biocorrodible magnesium alloys for temporary implants having filigree structures is made difficult in particular because degradation of the implant progresses very quickly in vivo. So as to reduce the corrosion rate, i.e., the degradation speed, different approaches are being discussed in the art. Modified alloys and coatings represent categories of approaches to reduce the corrosion rate of magnesium alloys. Some of the existing approaches show promise, but none of them has so far led to a commercially available product to the knowledge of the inventors. Regardless of the efforts made so far, there remains a need for solutions to at least temporarily reduce the corrosion of magnesium alloys in vivo, while optimizing the mechanical properties thereof at the same time.

SUMMARY OF THE INVENTION

Preferred embodiments of the invention provide a biodegradable magnesium alloy, a method for the production thereof and implants made from the alloy, which allow the magnesium matrix of the implant to remain in an electrochemically stable state over the required support period with fine grain and high corrosion resistance without protective layers, while also improving the mechanical properties, such as increasing the tensile strength and proof stress, as well as reducing the mechanical asymmetry.

A preferred magnesium alloy includes 1.5 to 7.0% by weight Zn, 0.5 to 3.5% by weight Al, the remainder being magnesium which contains impurities, which promote electrochemical potential differences and/or the formation of precipitations and/or intermetallic phases, in a total amount of no more than 0.0063% by weight of Fe, Si, Mn, Co, Ni, Cu, Zr, Y, Sc or rare earths having the ordinal numbers 21, 57 to 71 and 89 to 103, Be, Cd, In, Sn and/or Pb as well as P, wherein the alloy content of Zn in % by weight is greater than or equal to the alloy content of Al in % by weight.

A preferred method for producing a magnesium alloy having improved mechanical and electrochemical properties includes generating high-purity magnesium by vacuum distillation. A billet of the alloy is synthesized with the high purity magnesium according and high-purity Zn and Al in a composition of 1.5 to 7.0% by weight Zn, 0.5 to 3.5% by weight Al, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y and Sc or rare earths having the ordinal numbers 21, 57 to 71 and 89 to 103, Be, Cd, In, Sn and/or Pb as well as P, wherein the alloy content of Zn in % by weight is greater than or equal to the alloy content of Al in % by weight. The alloy is homogenized by annealing at a temperature between 250° C. and 350° C. with a holding period of 1 to 60 hours and cooled by exposure to air and in a water bath. The homogenized alloy is formed in the temperature range between 250° C. and 350° C., preferably 270° C. and 350° C. Preferably, the formed alloy is heat treated in the temperature range between 200° C. and 350° C. with a holding period of 5 minutes to 6 hours

DETAILED DESCRIPTION OF THE PREFERRED EMBODIMENTS

The magnesium alloy according to the invention has extraordinarily high corrosion resistance, which is achieved by drastically reducing the content of impurities and the combinations thereof in the magnesium matrix, and by also adding precipitation and solid solution hardenable elements, which must be present in completely solid solution. The microstructure that is obtained has no electrochemical potential differences between the individual matrix phases after the forming and heat treatment processes, and therefore these differences cannot expedite the corrosion in physiological media. The alloys according to the invention provide corrosion resistance and deformability of the magnesium matrix of an implant formed from the alloy, which must be assured over the support period such that the implant is able to absorb multiaxial permanent load without fracture or cracking, and to also utilize the magnesium matrix as a means for the decomposition triggered by the physiological liquids.

The applicant surprisingly found that an alloy matrix, which has a content of Zn of preferably 1.5 to 5.5% by weight, and more particularly 3.5 to 5.5% by weight, and a content of Al of preferably at least 0.5 to 2.0% by weight, and more particularly 1.0 to 2.0% by weight, can form, or depending on the treatment forms, a mixed crystal from Zn and Al, which are present completely in solution form, without precipitations, the mixed crystal having a higher standard potential than unalloyed high-grade magnesium and therefore the alloy being more noble.

Preferably, the alloy contents of Zn and Al are adjusted such that the content in solid solution is as high as possible, and therefore maximum corrosion protection is achieved, without exceeding the solubility limit. Typical forming temperatures for this alloy range between 270 and 330° C. under these conditions. This prevents particles from forming in the alloy matrix, which could take on the functions of cathodes during the corrosion process and thus promote corrosion.

Another surprising result is that, at a content of Zn of preferably 3.0 to 7.0% by weight, and more particularly 4.0 to 6.0% by weight, and a content of Al of preferably 0.5 to 3.5% by weight, and more particularly 1.5 to 2.5% by weight, an alloy is obtained which contains precipitations in the form of $Mg_3Zn_3Al_2$ and MgZn and has an extremely small grain size, wherein the precipitations having a size of less than 1 µm, and preferably 0.2 µm, are located both on the grain boundaries and in the grain interior.

In this case, the alloying elements may be present in the alloy in amounts even slightly above the solubility limit. Controlled by the cooling conditions during the production of the alloy, the alloying elements are initially present in solution. During forming of the alloy at temperatures below the solubility limit, for example at 250° C., fine particles are precipitated during forming which prevent grain growth and then contribute to an increase in tensile strength, both due to particle hardening and grain refining hardening. Through subsequent aging of the formed semi-finished product at temperatures below the temperature at which the alloying elements go completely into solution, for example 200° C., it is also possible to precipitate fine particles, which continue to remain in the matrix during the later thermomechanical treatment steps so as to prevent grain growth and increase the strength.

The alloy according to the invention has particularly high corrosion resistance. This is achieved by drastically reducing the contents of certain elements, and combinations of certain elements, in the alloy matrix whereby a microstructure is obtained in which, contrary to all known technically available magnesium materials, electrochemical differences in potential no longer occur between the individual matrix phases, and these therefore no longer play a role in terms of an expedited corrosion of the material in physiological media.

The previously known tolerance limits for impurities do not take into account that wrought magnesium alloys often times are subjected to a thermomechanical treatment, and more particularly to an extended annealing process, which creates near-equilibrium structures. The metallic elements bond by way of diffusion and form what are known as intermetallic phases, which have a different electrochemical potential, notably a considerably higher potential, than the magnesium matrix, and therefore these intermetallic phases act as cathodes and can trigger galvanic corrosion processes.

Because the alloy according to the invention contains Al, it is particularly important to limit not only elements such as Ni, Co or Cu, which in general have a considerable adverse effect on the corrosion resistance of magnesium alloys, but notably the elements Fe, Mn and Si.

When producing such an alloy according to the prior art, both a remainder of Fe and a remainder of Mn are left in the melt. In addition, such melts are not purified with respect to Si. However, Fe, Mn and Si have a very high tendency to form a ternary intermetallic Fe—Mn—Si phase, which has a very positive potential and thus constitutes a very effective cathode for the corrosion of the material. Moreover, Al additionally shifts the boundary in the melt at which iron begins to precipitate as iron particles or intermetallic particles with other elements toward drastically lower iron contents.

The applicant has found that a corrosion-stable alloy matrix can be achieved when complying with the following tolerance limits of individual impurities in % by weight: Fe, Si, Mn, Co, Ni, Cu each with <0.0005; Zr, Y each with <0.0003; Sc or rare earths having the ordinal numbers 21, 57 to 71 and 89 to 103 in total <0.001; Be, Cd, In, Sn and/or Pb each with <0.0003; and P<0.0002.

Preferably, the corrosion-stable alloy matrix contains impurities in a total amount of no more than 0.0053 Gew. %, which can be achieved when complying with the following tolerance limits of individual impurities in % by weight:

Fe, Si, Mn each with <0.0005; Co, Ni, Cu each with <0.0002; Zr, Y each with <0.0003; Sc or rare earths having the ordinal numbers 21, 57 to 71 and 89 to 103 in total <0.001; Be, Cd, In, Sn and/or Pb each with <0.0003; and P<0.0001.

In particular preferred embodiments, the corrosion-stable alloy matrix contains impurities in a total amount of no more than 0 0022 Gew. %, which can be achieved when complying with the following tolerance limits of individual impurities in % by weight:

Fe, Fe, Si, Mn each with <0.0002; Co, Ni, Cu, Zr, Y each with <0.0001; Sc or rare earths having the ordinal numbers 21, 57 to 71 and 89 to 103 in total <0.0005; Be, Cd, In, Sn and/or Pb each with <0.0001, and P <0.0001.

The formation of precipitations or particles which have a positive potential difference as compared to the matrix is entirely suppressed, or drastically reduced, if the sum of individual impurities consisting of Fe, Si, Mn, Co, Ni and Cu is no more than 0.0030% by weight, preferably no more than 0.0021% by weight, and particularly preferably no more than 0.0009% by weight.

The particular advantage of the alloy according to the invention is that it no longer has any relevant contents of Fe, Si or Mn and only Zn and Al remain in the material, which increase the corrosion resistance of magnesium and increase the strength, however no elements are present which could form effective cathodes for corrosion processes. Such low concentrations moreover no longer allow a formation of intermetallic phases, which have a more positive electrochemical potential as compared to the matrix.

Because the Zr content is considerably below that of the prior art, no Zr-rich phases can form, which are always more noble than the magnesium matrix and thus act as cathodic sites which promote corrosion.

By limiting the yttrium content, the tendency toward stress and vibration corrosion is advantageously decreased, counteracting a rapid weakening of the mechanical strength.

Because the chemical elements of a magnesium alloy from biodegradable implants are absorbed by the human body, additionally the amounts of highly toxic elements such as Be, CD, In, Sn and/or Pb as well as rare earths (elements having the ordinal numbers 21, 57 to 71 and 89 to 103) must be limited in the alloy so as to achieve high biocompatibility, while also suppressing the formation of intermetallic phases between these elements and magnesium, aluminum and zinc.

Such low concentrations thus also ensure that the magnesium matrix no longer contains any, or contains only small amounts of, precipitations or particle phases, which have a more positive electrochemical potential as compared to the matrix.

In the connection with solid solution hardening by Zn and Al, these precipitations or particles of the elements contained in the alloy according to the present application allow the tensile strength of the magnesium matrix to be increased and the electrochemical potential of the matrix to be raised, whereby a corrosion-decreasing effect is created, notably with respect to physiological media. The precipitations preferably have a size of no more than 1 µm, and preferably of no more than 0.2 µm, and are located on the grain boundaries and in the grain interior, whereby the movement of grain boundaries during thermal treatment as well as dislocations during deformation are impaired and the strength of the magnesium alloy is increased.

The magnesium alloy according to the present patent application achieves a tensile strength of >275 MPa, and preferably >300 MPa, a yield point of >200 MPa, and preferably >225 MPa, and a yield ratio of <0.8, and preferably <075, wherein the difference between the tensile strength and yield point is >50 MPa, and preferably >100 MPa, and the mechanical asymmetry is <1.25.

These significantly improved mechanical properties of the novel magnesium alloy assure that the implants, for example cardiovascular stents, are able to withstand the multiaxial permanent load in the implanted state over the entire support period, despite onsetting degradation of the magnesium matrix due to corrosion.

So as to minimize the mechanical asymmetry, it is particularly important for the magnesium alloy to have a particularly fine microstructure having a grain size of no more than 7.5 µm, preferably <5 µm, and particularly preferably <2.5 µm.

A method for producing a magnesium alloy having improved mechanical and electrochemical properties is provided. The method comprises the following steps:

a) generating high-purity magnesium by vacuum distillation;
b) generating a billet of the alloy by synthesis of the high-purity magnesium with high-purity Zn and Al in a composition of 1.5 to 7.0% by weight Zn, 0.5 to 3.5% by weight Al, the remainder being magnesium containing impurities, which promote electrochemical potential differences and/or the formation of precipitations and/or intermetallic phases, in a total amount of no more than 0.0063% by weight of Fe, Si, Mn, Co, Ni, Cu, Zr, Y and Sc or rare earths having the ordinal numbers 21, 57 to 71 and 89 to 103, Be, Cd, In, Sn and/or Pb as well as P, wherein the alloy content of Zn in % by weight is greater than or equal to the alloy content of Al in % by weight;
c) homogenizing the alloy by annealing at a temperature between 250° C. and 350° C. with a holding period of 1 to 60 hours and cooling by exposure to air and in a water bath;
c) at least single forming of the homogenized alloy in the temperature range between 250° C. and 350° C.; and
d) optionally heat treating the formed alloy in the temperature range between 200° C. and 350° C. with a holding period of 5 minute to 6 hours.

In a preferred embodiment, step c) is performed alloy in the temperature range between 270° C. and 350° C.

A content of Zn of preferably 1.5 to 5.5% by weight, and more particularly 3.5 to 5.5% by weight, and a content of Al of preferably at least 0.2 to 2.0% by weight, and more particularly 1.0 to 2.0% by weight, assures that the microstructure of the alloy is a mixed crystal made of Zn and Al, which are present completely in solution form, without precipitations, the mixed crystal having a higher standard potential than the high-grade magnesium. During subsequent forming, care must be taken that the forming temperature, for example 270° C. to 330° C., is adhered to so as to ensure that the solubility limit for the individual elements is not exceeded. This prevents particles from forming in the matrix, which can have a corrosion-accelerating effect.

In contrast, a content of Zn of preferably 3.0 to 7.0% by weight, and more particularly 4.0 to 6.0% by weight, and a content of Al of preferably 0.5 to 3.5% by weight, and more particularly 1.5 to 2.5% by weight means that the alloying element may be present in amounts slightly higher than the solubility limit. The shaping process, after homogenizing annealing, at temperatures of 200° C. to 350° C. below the solubility limit according to step d) prevents precipitations in the $Mg_{17}Al_{12}$ phase and causes only fine particles to be precipitated in the matrix in the form of $Mg_3Zn_3Al_2$ and MgZn, which impair grain growth and contribute to an increase in the tensile strength of the alloy due to particle hardening and grain refining hardening. Through subsequent aging of the formed semi-finished product below temperatures at which the alloying elements are caused to go completely into solution (typically, these are temperatures of 20° C. to 325° C.), it is possible to precipitate particles, which continue to remain in the matrix during the later thermomechanical treatment, prevent grain growth processes and further increase the strength.

Vacuum distillation is preferably used to produce a starting material for the alloy according to the present patent application having the required threshold values.

The quantities of the alloying elements Zn and Al as well as the sum of impurities can be selectively adjusted and in % by weight are:

a) for the individual impurities:
Fe, Si, Mn, Co, Ni, Cu each with <0.0005;
Zr, Y each with <0.0003;
Sc or rare earths having the ordinal numbers 21, 57 to 71 and 89 to 103 in total <0.001;
Be, Cd, In, Sn and/or Pb each with <0.0003; and
P<0.0002.

aa) for the individual impurities in a preferred total amount of impurities of no more than 0.0053% by weight:
Fe, Si, Mn each with <0.0005;
Co, Ni, Cu each with <0.0002;
Zr, Y each with <0.0003;
Sc or rare earths having the ordinal numbers 21, 57 to 71 and 89 to
103 in total <0.001;
Be, Cd, In, Sn and/or Pb each with <0.0003; and
P<0.0001.

ab) for the individual impurities in a particularly preferred total amount of impurities of no more than 0.0022% by weight:
Fe, Si, Mn each with <0.0002;
Co, Ni, Cu, Zr, Y each with <0.0001;
Sc or rare earths having the ordinal numbers 21, 57 to 71 and 89 to 103 in total <0.0005;
Be, Cd, In, Sn and/or Pb each with <0.0001; and
P<0.0001.

b) for the combination of individual impurities in total:
Fe, Si, Mn, Co, Ni and Cu no more than 0.0040, preferably no more than 0.0020, and particularly preferably no more than 0.0010.

It is particularly advantageous that the method described here only requires a small number of forming steps. Extrusion, equal channel angular extrusion and/or multiple forging can thus preferably be employed, which assure that a substantially homogeneous fine grain of <15 μm is achieved.

Because of the artificial aging, precipitations having a grain size of 1 μm, and preferably 0.2 μm, form on the grain boundaries and in the interior of the grains, whereby the tensile strength of the alloy reaches values which at >275 MPa, and preferably >300 MPa, are considerably higher than the prior art.

The magnesium alloy produced according to the method, which has the above described advantageous composition and structure, in medical technology, can also be used in the production of implants, for example endovascular implants such as stents, for fastening and temporarily fixing tissue implants and tissue transplantations, orthopedic and dental implants, and neuroimplants.

Particular implants of the invention are in the Cardiovascular field, osteosynthesis field or other areas.

Cardiovascular field in the sense of this application includes
the field of diagnostic, prevention and treatment of all diseases of the cardiovascular system, i.e. heart and blood vessel system,
by mean of active and non-active implants used to support vessels, and vein systems
including coronary, cerebral and peripheral vascular implants like stents, valves, closure devices, occluders, clips, coils, staples, implantable regional drug delivery devices, implantable electrostimulators (like pacemakers and defibrillators), implantable monitoring devices, implantable electrodes, system for fastening and temporarily fixing tissue implants and tissue transplantations
    field also includes any type of stent as mechanical fix or temporary scaffold to support hollow organs and structures including bones, intervertebral disks Osteosynthesis in the sense of this application includes
    the field of treatment of fractured bones for internal fixation and stabilization by mechanical devices such as metal plates, pins, rods, wires, screws, clips, nails, staples excluding stent technology Examples of areas out of the osteosynthesis field or the cardiovascular field are:

Devices for the treatment of diseases of the sinews, joints, muscles, cartilages, oral (including dental) and maxillo facial implants (excl. osteosynthesis means), esthetic implants, supporting tools out of the body, tissue engineering, soft tissue implants, devices for wound care, suture material and clamps, neurosurgery local drug delivery (excl. cardiovascular, i.e. lever)
renal

EXEMPLARY EMBODIMENTS

Example 1

A magnesium alloy includes 5% by weight Zn and 2% by weight Al, the remainder being Mg, in which the alloying elements are present completely in solution form, and which contains the following individual impurities in % by weight:

Fe: <0.0005; Si: <0.0005; Mn: <0.0005; Co: <0.0002; Ni: <0.0002; Cu<0.0002, wherein the sum of impurities consisting of Fe, Si, Mn, Co, Ni and Cu should be no more than 0.0021% by weight, the content of Zr<0.0003% by weight, the content of Y<0.0001% by weight, the content of rare earths having the ordinal numbers 21, 39, 57 to 71 and 89 to 103 in total should be less than 0.001% by weight, and the contents of Be and Cd should be no more than 0.0001% by weight, respectively, and P<0.0001.

This alloy, produced using magnesium vacuum distillation, is subjected to homogenizing annealing at a temperature of 300° C. for a duration of 48 hours, and subsequently to a forming process at a temperature of 275° C. to 300° C., which is above the solubility limit. A precision tube for a cardiovascular stent is produced by multiple extrusion and annealing processes above the solubility limit at 275° C. so as to prevent the precipitation of $Mg_3Zn_3Al_2$ particles.

The grain size that was achieved was <10 μm, and the magnesium alloy reached a tensile strength of more than 300 MPa and proof stress of <230 MPa. The yield ratio was 0.72 and the mechanical asymmetry was 1.15.

Example 2

A magnesium alloy includes 5.5% by weight Zn and 3% by weight Al, the remainder being magnesium, in which some of the alloying elements are present as particles in the form of MgZnAl having a size of <0.5 μm, and which contains the following individual impurities in % by weight:

Fe: <0.0005; Si: <0.0005; Mn: <0.0005; Co: <0.0002; Ni: <0.0002; Cu<0.0002, wherein the sum of impurities consisting of Fe, Si, Mn, Co, Ni and Cu should be no more than 0.0021% by weight, the content of Zr<0.0003% by weight, the content of Y<0.0001% by weight, the content of rare earths having the ordinal numbers 21, 39, 57 to 71 and 89 to 103 in total should be less than 0.001% by weight, and the contents of Be and Cd should be no more than 0.0001% by weight, respectively, and P<0.0001.

The magnesium alloy is produced in a manner which corresponds to that of Example 1. So as to precipitate some of the MgZnAl particles, an extrusion process is carried out above the solubility limit at temperatures of ≤275° C.

The precision tubes for a cardiovascular stent were produced by multiple extrusion and annealing processes, in part below the solubility limit. The solubility limit was 330° C. This alloy according to the subject matter of the patent application reached the following properties:

tensile strength of 310 to 340 MPa;

proof stress of ≤230 MPa;

a yield ratio of 0.69;

mechanical asymmetry of 1.1; and a grain size of <5 μm.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A biodegradable implant formed from a magnesium alloy, the magnesium alloy comprising:
1.5 to 5.5% by weight Zn, 0.5 to 2% by weight Al, the remainder being high-purity vacuum distilled magnesium defining an alloy matrix having solid solutions of Al and/or Zn and intermetallic phases of magnesium and Al in the alloy matrix, the matrix lacking Mn as an alloying element to suppress formation of the ternary intermetallic phase FeMnSi, the magnesium alloy containing a total amount of no more than 0 0063% by weight of impurities selected from the group including Fe, Si, Mn, Co, Ni, Cu, Zr, Y, Sc, lanthanoids, actinoids, Be, Cd, In, Sn, Pb, and P, wherein the alloy content of Zn in % by weight is greater than or equal to the alloy content of Al in % by weight, wherein the magnesium alloy contains precipitations in the form of $Mg_3Zn_3Al_2$ and MgZn.

2. The implant according to claim 1, wherein the content of Zn is 3.0 to 5.5% by weight, and the content of Al is 0.5 to 2% by weight.

3. The implant according to claim 1, wherein individual impurities in the total sum of impurities amount to the following in % by weight: Fe<0.0005; Si<0.0005; Mn<0.0005; Co<0.0005; Ni<0.0005; Cu<0.0005; Zr<0.0003; Y<0.0003; Sc or rare earths having the ordinal numbers 21, 57 to 71 and 89 to 103 in total <0.001; Be, Cd, In, Sn and/or Pb each with <0.0003; and P<0.0002.

4. The implant according to claim 1, wherein impurity elements Fe, Si, Mn, Co, Ni, and Cu together total no more than 0 0030% by weight.

5. The implant according to claim 4, wherein impurity elements Fe, Si, Mn, Co, Ni, and Cu together total no more than 0 0021% by weight.

6. The implant according to claim 5, wherein impurity elements Fe, Si, Mn, Co, Ni, and Cu together total no more than 0 0009% by weight.

7. The implant according to claim 1, wherein the alloy has a fine-grained microstructure having a grain size of <7.5 µm, without considerable electrochemical potential differences between the individual alloy matrix phases.

8. The implant according to claim 1, wherein the magnesium alloy contains only such precipitations which have no potential differences, or potential differences as small as possible, as compared to the alloy matrix, or which are less noble than the alloy matrix.

9. The implant according to claim 1, wherein the precipitations have a size of ≤1 µm, and are dispersedly distributed at the grain boundaries or in the grain interior.

10. The implant according to claim 1, wherein the mechanical asymmetry is <1.25.

11. The implant according to claim 1, having a tensile strength of ≥300 MPa, a yield point of ≥225 MPa, and a yield ratio of <0.75, wherein the difference between the tensile strength and yield point is >100 MPa, and the mechanical asymmetry is <1.25.

12. The implant according to claim 1, wherein the content of Zn is 3.5 to 5.5% by weight, and the content of Al is 1.0 to 2.0% by weight.

13. The implant according to claim 1, wherein the content of Zn is 4.0 to 5.5% by weight, and the content of Al 1.5 to 2% by weight.

14. The implant according to claim 1, wherein the alloy matrix has a fine-grained microstructure <2.5 µm, without considerable electrochemical potential differences between the individual matrix phases.

15. The implant according to claim 1, wherein the precipitations have a size of <0.2 µm, and are dispersedly distributed at the grain boundaries or in the grain interior.

16. The implant according to claim 1, wherein the magnesium alloy forms a body of a cardiovascular implant or osteosynthesis implant.

17. The implant according to claim 1, wherein the content of Zn is 1.5 to 3.5% by weight.

18. The implant according to claim 1, wherein the precipitations are dispersedly distributed at the grain boundaries or in the grain interior.

19. The implant according to claim 1, comprising one of an endovascular implant, a stent, implants for fastening and temporarily fixing tissue implants and tissue transplantations, orthopedic implant, dental implant, and neuroimplant.

* * * * *